United States Patent [19]

Holmwood et al.

[11] Patent Number: 4,960,453
[45] Date of Patent: * Oct. 2, 1990

[54] HYDROXYALKYL-AZOLYL DERIVATIVES AS FUNGICIDES AND PLANT GROWTH REGULATORS

[75] Inventors: Graham Holmwood, Wuppertal; Gerhard Jäger, Leverkusen; Karl H. Büchel, Burscheid; Wilhelm Brandes, Leichlingen; Stefan Dutzmann, Duesseldorf; Gerd Hänssler, Leverkusen, all of Fed. Rep. of Germany

[73] Assignee: Bayer Aktiengesellschaft, Leverkusen, Fed. Rep. of Germany

[*] Notice: The portion of the term of this patent subsequent to Jan. 16, 2007 has been disclaimed.

[21] Appl. No.: 190,601

[22] Filed: May 5, 1988

[30] Foreign Application Priority Data

May 18, 1987 [DE] Fed. Rep. of Germany ....... 3716558

[51] Int. Cl.$^5$ .................. A01N 43/653; C07D 249/08
[52] U.S. Cl. ........................... 71/92; 71/76; 514/184; 514/383; 548/267.8; 548/268.6
[58] Field of Search ...................... 71/92, 76; 514/383, 514/184; 548/262, 101, 267.8

[56] References Cited

U.S. PATENT DOCUMENTS

| | | | |
|---|---|---|---|
| 4,549,900 | 10/1985 | Kramer et al. | 548/262 |
| 4,723,984 | 2/1988 | Holmwood et al. | 548/262 |
| 4,734,126 | 3/1988 | Holmwood et al. | 548/262 |

FOREIGN PATENT DOCUMENTS

| | | |
|---|---|---|
| 0061835 | 10/1982 | European Pat. Off. . |
| 0091398 | 10/1983 | European Pat. Off. . |
| 0040345 | 7/1984 | European Pat. Off. . |
| 0181529 | 5/1986 | European Pat. Off. . |

OTHER PUBLICATIONS

Reinecke et al., "Bay Hw6 1608, a new etc" CA 106: 151484u (1987).

Primary Examiner—Glennon H. Hollrah
Assistant Examiner—Patricia L. Morris
Attorney, Agent, or Firm—Sprung Horn Kramer & Woods

[57] ABSTRACT

Fungicidal and plant growth-regulating hydroxyalkylazolyl derivatives of the formula

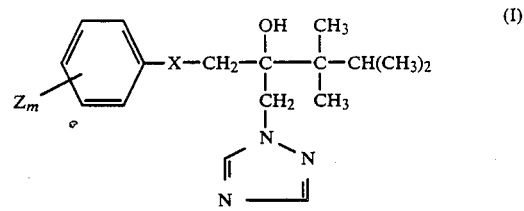

in which Z represents halogen, alkyl with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms, phenyl or alkoximinomethyl with 1 to 4 carbon atoms in the alkoxy group, X represents oxygen, sulphur or a $CH_2$ group and m represents the number 0, 1, 2 or 3, and addition products thereof with acids and metal salts. Intermediates of the formulas

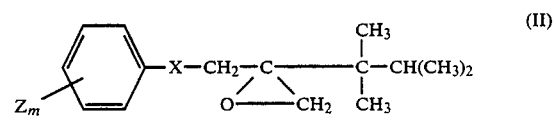

and

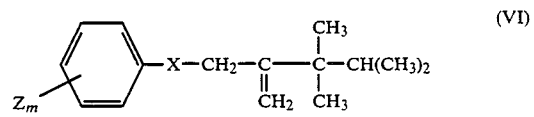

are also new.

5 Claims, No Drawings

HYDROXYALKYL-AZOLYL DERIVATIVES AS FUNGICIDES AND PLANT GROWTH REGULATORS

The present invention relates to new hydroxyalkylazolyl derivatives, a process for their preparation and also their use as fungicides and plant growth regulators.

It has already been disclosed that numerous hydroxyalkyl-azolyl derivatives possess fungicidal and plant growth regulatory properties (compare EP-OS (European Published Specification) No. 0,040,345 and EP-OS (European Published Specification) No. 0,061,835). Thus, for example, 2-(4-chloro-phenoxy-methyl)-3,3-dimethyl-1-(1,2,4-triazol-1-yl)-butan-2-ol and 1-(4-chlorophenyl)-4,4-dimethyl-3-(1,2,4-triazol-1-yl-methyl)-pentan-3-ol can be used for combating fungi and for regulating the growth of plants. The activity of these compounds is in general very good; however, the plant tolerance and also the activity leave something to be desired in some cases.

New hydroxyalkyl-azolyl derivatives of the formula

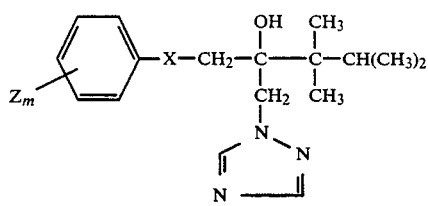

in which
- Z represents halogen, alkyl with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms, phenyl or alkoximinomethyl with 1 to 4 carbon atoms in the alkoxy group,
- X represents oxygen, sulphur or a CH$_2$ group and
- m represents the numbers 0, 1, 2 or 3, and their acid addition salts and metal salt complexes have now been found.

The new hydroxyalkyl-azolyl derivatives of the formula (I) possess an asymmetrically substituted carbon atom and can therefore exist in two optical isomeric forms. The invention relates to both the racemates and also to the individual isomers and their mixtures.

Furthermore, it has been found that hydroxyalkylazolyl derivatives of the formula (I), as well as their acid addition salts and metal salt complexes, are obtained when oxiranes of the formula

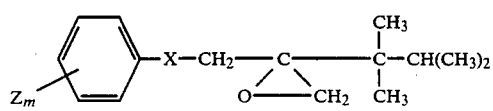

in which
X, Z and m have the abovementioned meaning, are reacted with 1,2,4-triazole of the formula

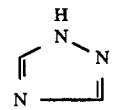

in the presence of a diluent and if appropriate in the presence of an acid binding agent and if appropriate in the presence of a catalyst and then if appropriate an acid or a metal salt is subsequently adducted to the compounds obtained thus of the formula (I).

Finally, it has been found that the hydroxyalkylazolyl derivatives of the formula (I) and their acid addition salts and metal salt complexes are distinguished by very good fungicidal and plant growth regulatory properties.

Surprisingly, the compounds according to the invention possess a better fungicidal and plant growth regulatory activity than 1-(4-chlorophenoxy-methyl)-3,3-dimethyl-1-(1,2,4-triazol-1-yl)-butan-2-ol and 1-(4-chlorophenyl)-4,4-dimethyl-3-(1,2,4-triazol-1-yl)-methyl)-pentan-3-ol, which are constitutionally similar, previously known active compounds with an equivalent type of action. In addition the compounds according to the invention exhibit an outstanding tolerance to plants.

Formula (I) gives a general definition of the hydroxyalkyl-azolyl derivatives according to the invention. Preferred compounds of the formula (I) are those in which
- X represents oxygen, sulphur or a CH$_2$ group,
- Z represents fluorine, chlorine, bromine, methyl, ethyl, trifluoromethyl, trifluoromethoxy, trifluoromethylthio, phenyl, methoximinomethyl or ethoximinomethyl and
- m represents the numbers 0, 1, 2 or 3.

When m represents 2 or 3, the substituents for Z can be identical or different.

Addition products of acids and those hydroxyalkylazolyl derivatives of the formula (I), in which X, Z and m have those meanings which have already been mentioned as preferred for these substituents or this index in connection with the description of the compounds according to the invention are also preferred compounds according to the invention.

The acids which can be added preferably include hydrohalic acids, such as, for example, hydrochloric acid and hydrobromic acid, in particular hydrochloric acid, furthermore phosphoric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids such as, for example, p-toluenesulfonic acid and 1,5-naphthalenedisulphonic acid.

Addition products of acids of metals of main groups II to IV and of subgroups I and II and also IV to VIII of the periodic table of the elements and those hydroxyalkyl-azolyl derivatives of the formula (I), in which X, Z and m have those meanings which have already been mentioned as preferred for these substituents or this index in connection with the description of the compounds according to the invention are additionally preferred compounds according to the invention.

Salts of copper, zinc, manganese, magnesium, tin, iron and nickel are particularly preferred here. Possible anions of these salts are those which are derived from those acids which lead to addition products which are physiologically tolerated by plants. In this connection, particularly preferred acids of this type are the hydrohalic acids, such as, for example, hydrochloric acid and hydrobromic acid, furthermore phosphoric acid, nitric acid and sulphuric acid.

The compounds given in the following table may be mentioned as examples for compounds according to the invention.

TABLE (I)

$$\underset{Z_m}{\text{[phenyl]}}-X-CH_2-\underset{\underset{N\diagdown N}{\overset{\overset{|}{CH_2}}{\underset{|}{C}}}}{\overset{\overset{|}{OH}}{\underset{|}{C}}}-\underset{\underset{CH_3}{|}}{\overset{\overset{CH_3}{|}}{C}}-CH(CH_3)_2$$

| X   | $Z_m$         |
|-----|---------------|
| O   | 4-F           |
| S   | 4-F           |
| CH₂ | 4-F           |
| O   | 2,4-Cl₂       |
| S   | 2,4-Cl₂       |
| CH₂ | 2,4-Cl₂       |
| O   | 4-CH₃         |
| S   | 4-CH₃         |
| CH₂ | 4-CH₃         |
| O   | 4-CF₃         |
| S   | 4-CF₃         |
| CH₂ | 4-CF₃         |
| O   | 4-CH=N—OCH₃   |
| S   | 4-CH=N—OCH₃   |
| CH₂ | 4-CH=N—OCH₃   |
| O   | 4-OCF₃        |
| S   | 4-OCF₃        |
| CH₂ | 4-OCF₃        |
| CH₂ | —             |
| O   | 4-CH=NOC₂H₅   |
| S   | 4-CH=NOC₂H₅   |
| CH₂ | 4-CH=NOC₂H₅   |

If 2-[2-(4-chlorophenyl)-ethyl]-2-[(1,1,2-trimethyl)-propyl]-oxirane and 1,2,4-triazole are used as starting materials, then the course of the process according to the invention can be represented by the following equation:

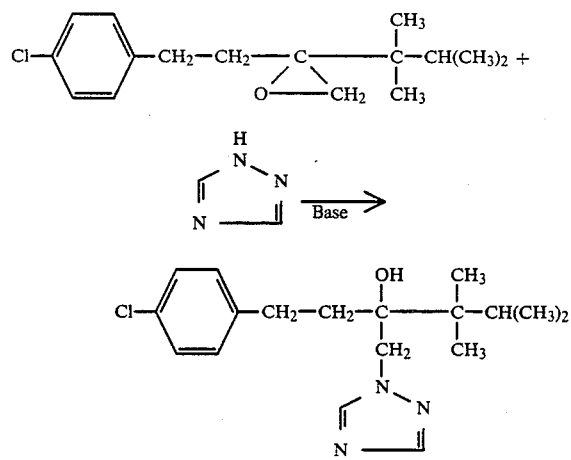

Formula (II) provides a general definition of the oxiranes to be used as starting substances in carrying out the process according to the invention. In this formula, X, Z and the index m preferably have those meanings, which have already been mentioned as preferred for these substituents or for the index m in connection with the description of the compounds of the formula (I) according to the invention.

The oxiranes of the formula (II) were hitherto not known. They can be prepared, in that, (a) in a first step, ketones of the formula

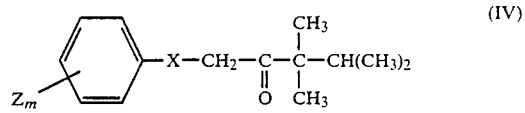

in which

X, Z and m have the abovementioned meaning, are reacted with methyl-triphenyl-phosphonium bromide of the formula

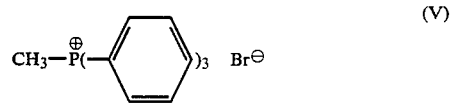

in the presence of a base and in the presence of a diluent and, (b) in a second step, the compounds thus obtained of the formula

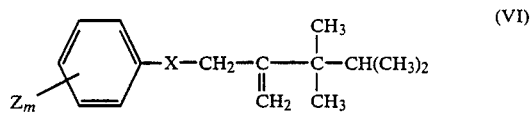

in which

X, Z and m have the abovementioned meaning, are reacted with peracids in the presence of a diluent.

The ketones of the formula (IV) required as starting substances in the preparation of the oxiranes of the formula (II) are known or can be readily prepared by processes which are known in principle (compare EP-OS (European Published Specification) No. 0,084,834). Thus those ketones of the formula (IV) in which X represents CH₂ are obtained by reacting the ketone of the formula

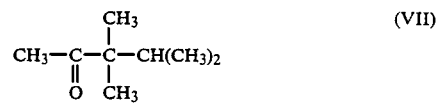

with aldehydes of the formula

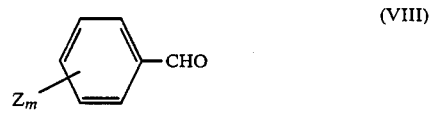

in which

Z and m have the abovementioned meaning, in the presence of a diluent, such as, for example, ethanol, at temperatures between 0° and 80° C. and hydrogenating the resultant compounds of the formula

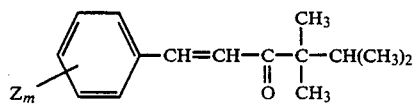

(IX)

in which

Z and m have the abovementioned meaning, using hydrogen in the presence of a catalyst, such as for example Raney nickel, in the presence of a diluent, such as, for example, toluene, at temperatures between 40° and 180° C.

In addition, those ketones of the formula (IV) in which X represents oxygen or sulphur can be prepared in that halogenoketones of the formula

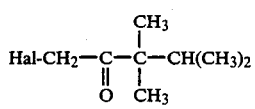

(X)

in which

Hal represents chlorine or bromine, are reacted with phenols or thiophenols of the formula

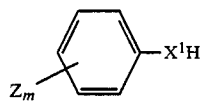

(XI)

in which

X$^1$ represents oxygen or sulphur and

Z and m have the abovementioned meaning, in the presence of a base and in the presence of a diluent, such as, for example, acetone, at temperatures between 10° and 120° C.

The methyl-triphenyl-phosphonium bromide of the formula (V) furthermore required as a starting material in the preparation of the oxiranes of the formula (II) is known.

The compounds of the formula (VI) required as starting substances in the second step in the preparation of the oxiranes of the formula (II) by the above process were hitherto unknown.

In the process for the preparation of the oxiranes of the formula (II), the first step is carried out in the presence of a base. Possible bases are all bases conventionally utilizable for Wittig reactions of this type. Potassium tert.-butylate is preferably utilizable.

In carrying out the first step of the above process for the preparation of the oxiranes of the formula (II), suitable diluents are all the organic solvents customary for reactions of this type. Aromatic hydrocarbons, such as benzene, toluene and xylene are preferably utilizable.

In carrying out the second step of the above process for the preparation of the oxiranes of the formula (II), possible reagents for the epoxidation are all customary peracids. Meta-chloroperbenzoic acid and peracetic acid are preferably utilizable. In addition, it is also possible to employ a mixture of acetic acid and hydrogen peroxide.

In carrying out the second step of the above process for the preparation of the oxiranes of the formula (II), suitable diluents are all the solvents customary for such epoxidations. Dichloromethane, toluene and chlorobenzene are preferably utilizable.

The reaction temperatures can be varied within a certain range in carrying out the process for the preparation of the oxiranes of the formula (II). In general, the first step is carried out at temperatures between 50° C. and 140° C. preferably between 80° C. and 120° C. The second step is generally carried out between 10° C. and 60° C, preferably between 20° C. and 50° C.

In carrying out the process for the preparation of the oxiranes of the formula (II), a procedure is generally followed in which, in the first step, between 1 and 3 mols of methyl-triphenylphosphonium bromide of the formula (V) and between 1 and 3 mols of a base are employed per mol of ketone of the formula (IV). In the second step, between 1 and 2 mols of peracid are in each case employed per mol of a compound of the formula (VI) Working up in each case is according to customary methods.

Those oxiranes of the formula (II) in which X represents oxygen or sulphur, can be prepared in that (c) ketones of the formula

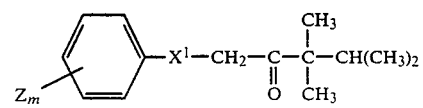

(IVa)

in which

Z and m have the abovementioned meaning and

X$^1$ represents oxygen or sulphur, are reacted either

α) with dimethyloxosulphonium methylide of the formula

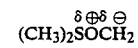

(XII)

or

β) with dimethylsulphonium methylide of the formula

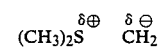

(XIII)

in the presence of a diluent.

The dimethyloxosulphonium methylide of the formula (XII) required as a reaction component in process (c) is known (compare J. Amer. Chem. Soc. 87, 1363 (1965)) It is used in the above reaction in the freshly prepared state, in that it is obtained in situ by reaction of trimethyl-oxo-sulphonium iodide with sodium hydride or sodium amide, in particular with potassium tert.-butylate or sodium methylate, in the presence of a diluent.

The dimethylsulphonium methylide of the formula (XIII) additionally possible as a reaction component in the process (c) is also known (compare Heterocycles 8, 397 (1977)). It is also employed in the above reaction in the freshly prepared state, in that it is obtained in situ, for example, from trimethylsulphonium halide or trimethylsulphonium methylsulphate, in the presence of a strong base, such as, for example, sodium hydride, sodium amide, sodium methylate, potassium tert.-butylate or potassium hydroxide, in the presence of a diluent, such as tert.-butanol or dimethyl sulphoxide.

In carrying out process (c), suitable diluents are inert organic solvents Alcohols, such as tert.-butanol, ethers, such as tetrohydrofuran or dioxane, furthermore aliphatic and aromatic hydrocarbons, such as benzene, toluene or xylene, and strongly polar solvents, such as dimethyl sulphoxide, are preferably utilizable.

The reaction temperatures can be varied within a relatively wide range in process (c). In general, the reaction is carried out at temperatures between 0° and 100° C., preferably between 10 and 60° C.

In carrying out the process (c), 1 to 3 mols of dimethyloxosulphonium methylide of the formula (XII) or of dimethylsulphonium methylide of the formula (XIII) are preferably employed per mol of ketone of the formula (IVa). The isolation of the oxiranes is according to customary methods.

The oxiranes of the formula (II) can, if appropriate, be directly reacted further without isolation in the process according to the invention.

Suitable diluents for the process according to the invention are organic solvents which are inert under the reaction conditions. Alcohols, such as, for example, ethanol, methoxyethanol or propanol; ketones, such as, for example, 2-butanone; nitriles, such as, for example, acetonitrile; esters, such as, for example, ethylacetate; ethers, such as, for example, dioxane; aromatic hydrocarbons, such as, for example, benzene and toluene; or amides, such as, for example, dimethylformamide, are preferably utilizable. It can also be of advantage to add a small quantity of water thereto.

Possible bases for the process according to the invention are all conventionally utilizable inorganic and organic bases. Alkali metal carbonates, such as, for example, sodium carbonate and potassium carbonate; alkali metal hydroxides, such as, for example, sodium hydroxide; alkali metal alcoholates, such as, for example, sodium methylate and potassium methylate, and sodium ethylate and potassium ethylate; alkali metal hydrides, such as, for example, sodium hydride; and also lower tertiary alkylamines, cycloalkylamines and aralkylamines, such as triethylamine in particular, are preferably utilizable.

In carrying out the process according to the invention all reaction accelerators customary for such reactions can be employed as catalysts. α, α′-azoisobutyronitrile is preferably utilizable.

The reaction temperatures can be varied over a relatively wide range in carrying out the process according to the invention. In general, the reaction is carried out at temperatures between 0° and 200° C., preferably between 60° and 150° C.

In carrying out the process according to the invention, the reaction is generally performed at atmospheric pressure. However, it is also possible to work at elevated or reduced pressure.

In carrying out the process according to the invention, 1 to 2 mols of 1,2,4-triazole and, if appropriate, 1 to 2 mols of acid binding agent are preferably employed per mol of oxirane of the formula (II). Working up and isolation of the final products are according to customary methods.

The compounds of the formula (I) obtainable according to the process according to the invention can be converted into acid addition salts or metal salt complexes.

For the preparation of acid addition salts of the compounds of the formula (I), preferably suitable acids are those which have already been mentioned as preferred acids in connection with the description of the acid addition salts according to the invention.

The acid addition salts of the compounds of the formula (I) can be obtained in a simple manner by customary salt formation methods, for example by dissolving a compound of the general formula (I) in a suitable inert solvent and adding the acid, for example hydrochloric acid, and can be isolated in a known manner, for example by filtering off, if necessary, and purified by washing with an inert organic solvent.

For the preparation of metal salt complexes of the compounds of the general formula (I), suitable salts of metals are preferably those which have already been described above.

The metal salt complexes of compounds of the general formula (I) can be obtained in a simple manner by customary processes, for example by dissolving the metal salt in alcohol, for example ethanol, and adding it to compounds of the general formula (I). Metal salt complexes can be isolated in a known manner, for example by filtering off, and purified, if necessary, by recrystallization The active compounds according to the invention exhibit a strong microbicidal action and can be employed as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as *Xanthomonas oryzae;* Pseudomonas species, such as *Pseudomonas lachrymans;* Erwinia species, such as *Erwinia* amylovora; Pythium species, such as *Pythium* ultimum; Phytophthora species, such as *Phytophthora infestans;* Pseudoperonospora species, such as *Pseudoperonospora humuli* or *Pseudoperonospora cubense;* Plasmopara species, such as *Plasmopara viticola;* Peronospora species, such as *Peronospora* pisi or *P. brassicae;* Erysiphe species, such as *Erysiphe graminis;* Sphaerotheca species, such as *Sphaerotheca fuliginea:* Podosphaera species, such as *Podosphaera leucotricha;* Venturia species, such as *Venturia inaequalis;* Pyrenophora species, such as *Pyrenophora teres* or *P. graminea* (conidia form: Drechslera, syn: Helminthosporium); Cochliobolus species, such as *Cochliobolus sativus* (conidia form: Drechslera, syn: Helminthosporium); Uromyces species, such as *Uromyces appendiculatus;* Puccinia species, such as *Puccinia recondita;* Tilletia species, such as *Tilletia caries;* Ustilago species, such as *Ustilago nuda* or *Ustilago avenae;* Pellicularia species, such as *Pellicularia sasakii:* Pyricularia species, such as *Pyricularia oryzae;* Fusarium species, such as *Fusarium culmorum;* Botrytis species, such as *Botrytis cinerea;* Septoria species, such as *Septoria nodorum;* Leptosphaeria species, such as *Leptosphaeria nodorum:* Cercospora species, such as *Cercospora canescens;* Alternaria species, such as *Alternaria brassicae* and Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The substances according to the invention can be employed with particularly good effect for combating rice diseases, such as Pellicularia sasakii and Pyricularia oryzae. Moreover they are very suitable for combating Puccinia recondita, Cochliobolus sativus and Leptosphaeria nodorum.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soybeans or cereals. Using growth regulators it is also possible, for example, to inhibit the degradation of desired constituents, such as, for example, sugar in sugar beets or sugar cane, before or after harvesting. It is also possible favorably &o influence the production or the efflux of secondary plant constituents. The stimulation of latex flux in rubber trees may be mentioned as an example.

Parthenocarpous fruit can be formed under the influence of growth regulators Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce Very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surfaceactive agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene-fatty acid esters, polyoxyethyl-ene-fatty alcohol ethers, for example alkylaryl polyglycol ethers, alkylsulphonates, alkylsulphates, arylsulphonates as well as albumin hydrolysis products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5° and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the compounds according to the invention are used as fungicides the amount applied can be varied within a relatively wide range depending upon the type of application. Thus, the active compound concentrations in the use forms for the treatment of plant parts are generally between 1 and 0.0001 % by weight, preferably between 0.5 and 0.001%. In the treatment of seeds, amounts of active substance of 0.001 to 50 g per kilogram of seed, preferably 0.01 to 10 g, are required. In the treatment of the soil active substance concentrations of 0.00001 to 0.1 % by weight, preferably 0.0001 to 0.02%, are required at the site of action.

When the compounds according to the invention are used as plant growth regulators, the amounts applied can be varied within a substantial range. In general, 0.01 to 50 kg, preferably 0.05 to 10 kg, of active compound are used per hectare of soil surface.

When the compounds according to the invention are used as plant growth regulators, the rule is that the growth regulators are applied within a preferred period of time, the exact definition of which depends on the climatic and vegetative circumstances.

The preparation and the use of the substances according to the invention can be seen from the following examples.

Preparation examples

Example 1

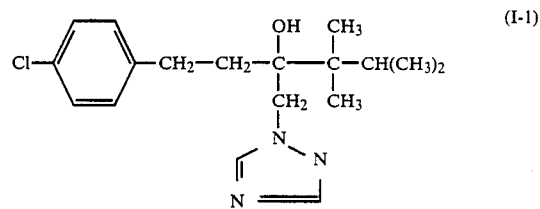

(I-1)

A solution of 14.0 g (0.052 mol) of 2-(4-chlorophenylethyl)-2-(1,1,2-trimethyl-propyl)-oxirane, 6.9 g (0.1 mol) of 1,2,4-triazole, 0.4 g of sodium hydroxide, 0.4 ml of water and a spatula tip full of α,α-azo-isobutyro-nitrile in 60 ml of dimethylformamide is heated at 120° C. for 10 hours After this, the solution is cooled to room temperature and concentrated by stripping off the solvent under reduced pressure, the residue remaining is dissolved in dichloromethane, the solution is washed three times with water, the organic phase is dried over sodium sulphate and the solvent is removed under reduced pressure. The residue is purified by column chromatography (silica gel; dichloromethane:ethyl acetate =1:1). In this manner, 8 1 g (46% of theory) of 1-(4-chlorophenyl)-3-(1,2,4-triazol-1-yl-methyl)-4,4,5-trimethyl-hexan-3-ol are obtained in the form of a solid substance, which has a melting point of 76°–78° C. after recrystallization from diisopropyl ether.

Preparation of starting materials

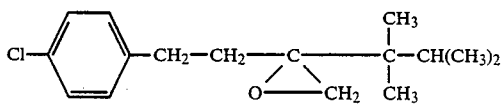

A solution of 11.7 g (0.068 mol) of m-chloroperbenzoic acid in 150 ml of dichloromethane is added dropwise to a boiling solution of 14.5 g (0.0579 mol) of 2-(4-chlorophenylethyl)-3,3,4-trimethyl-pent-1-ene in 60 ml of dichloromethane over the course of 1.5 hours. The solution is heated under reflux for a further 4 hours, then cooled to room temperature and initially washed three times with 1N aqueous sodium hydroxide solution and thereafter with water, and the organic phase is then dried over sodium sulphate and concentrated by stripping off the solvent under reduced pressure 14.0 g of a yellow oil are obtained, which, according to gas chromatographic and mass spectrometric analysis, consists to 88% of 2-(4-chlorophenylethyl)-2-(1,1,2-trimethylpropyl)oxirane. The yield is accordingly calculated as 80% of theory. The product is used for further reaction without additional purification.

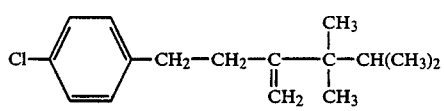

A suspension of 47.4 g (0.133 mol) of methyltriphenyl-phosphonium bromide and 15.3 g (0.137 mol) of potassium tert.-butylate in 250 ml of absolute toluene is heated under reflux under dry nitrogen 25.2 g (0.1 mol) of 1-(4-chlorophenyl)-4,4,5-trimethyl-hexan-3-one are introduced over the course of 5 minutes The reaction mixture is heated under reflux for a further 15 hours, then cooled to room temperature, washed twice with water and concentrated under reduced pressure The residue is taken up in ethyl acetate, cooled to 5° C. and the crop of crystals formed is filtered off with suction. The filtrate is concentrated and distilled under reduced pressure. 14.5 g (58% of theory) of 2-(4-chlorophenylethyl)-3,3,4-trimethyl-pent-1-ene are obtained in the form of a yellow oil of boiling point 88°–90° C./0.1 mbar.

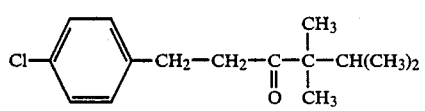

5 g of Raney nickel are added to a solution of 33.1 g (0.132 mol) of 1-(4-chloro-phenyl)-4,4,5-trimethyl-1-hexen-3-one in 200 ml of toluene and the mixture is stirred in an autoclave for 5 hours at 80° C. under a hydrogen pressure of 80–100 bar. After this, the reaction mixture is filtered and concentrated under reduced pressure. 28.3 g (85% of theory) of 1-(4-chlorophenyl)-4,4,5-trimethyl-hexan-3-one are obtained in the form of a yellow oil.

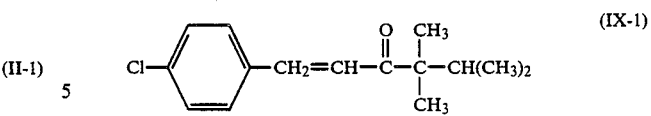

44.4 g (0.316 mol) of 4-chlorobenzaldehyde and 40 5 g (0.316 mol) of 3,3,4-trimethyl-pentan-2-one are dissolved in a mixture of 100 ml of ethanol and 10 ml of water, and a solution of 0.9 g of sodium hydroxide in 10 ml of water is added. The mixture is initially stirred for 1 hour at room temperature, then 0.4 g of solid sodium hydroxide is added and the mixture is stirred for a further 16 hours. The precipitate which results is filtered off with suction and then washed with water. 33.1 g (42% of theory) of 1-(4-chlorophenyl)-4,4,5-trimethyl-1-hexen-3-one are obtained in the form of a low melting, oily-crystalline product.

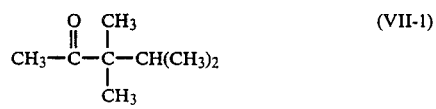

97.2 g (0.6 mol) of 1-chloro-3,3,4-trimethylpentan-2-one are added to a solution of 209 g (1.2 mols) of sodium dithionite and 540 g (6 mols of sodium hydrogen carbonate in a mixture of 1liter of dimethylformamide and 1 liter of water. The mixture is stirred at 70° C. for 1 hour. After this, the reaction mixture is filtered, the solid is washed with ether and the filtrate is extracted twice with ether. The combined ether phases are washed twice with water and concentrated under reduced pressure after drying over sodium sulphate. 42 g of a colorless liquid are obtained, of which, according to gas chromatographic analysis, more than 90% consists of 3,3,4-trimethyl-pentan-2-one. The yield is calculated thereafter as 49% of theory.

Example 2

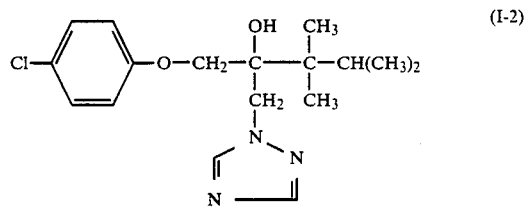

376 g of crude 2-(4-chlorophenoxymethyl)-2-(1,1,2-trimethylpropyl)-oxirane dissolved in 400 ml of n-butanol are added dropwise to a boiling solution of 13.4 g (0.14 mol) of sodium butanolate and 97 g (1.4 mols of 1,2,4-triazole in 400 ml of n-butanol in 1.5 hours. After boiling under reflux for 22 hours, the solvent is removed by distillation under reduced pressure and 500 ml of dichloromethane are added to the residue. Precipitated 2-(4-chlorophenoxymethyl)-1-(1,2,4-triazol-4-yl)-3,3,4-trimethylpentan-2-ol (15 g; melting point 173°–174° C.) is filtered off from the mixture, the filtrate is washed twice with 250 ml of water each time and dried over anhydrous sodium sulphate and the solvent is removed by distillation. The residue is chromatographed on silica gel using trichloromethane as eluant. 174 g of 2-(4-chlorophenoxymethyl)-1-(1,2,4-triazol-1-yl)-3,3,4- trimethylpentan-2-ol are thus obtained in the form of colorless crystals of melting point 59°-60° C.

Preparation of starting materials

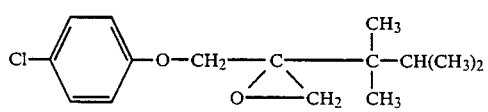
(II-2)

285 ml (3 mols of dimethyl sulphate are added dropwise over 1.5 hours at 20°-30° C. with external cooling to a solution of 220 ml (3 mols of dimethyl sulphide in 488 ml of tert.-butanol. The mixture is stirred at 20°-25° C. for a further 3 hours, then 382.2 g (1.5 mols) of 1-(4-chlorophenoxy)-3,3,4-trimethylpentan-2-one dissolved in 380 ml of tert.-butanol are added and 336 g (6 mols of powdered potassium hydroxide are subsequently introduced at 20°-30° C. with external cooling over the course of 1 hour. After 16 hours, 375 ml of toluene and 375 ml of water and also 187 ml of chlorine water are added. The organic phase is separated off, washed three times with 1,000 ml of water each time, dried over anhydrous sodium sulphate and evaporated under reduced pressure. The crude 2-(4-chlorophenoxymethyl)-2-(1,1,2-trimethylpropyl)-oxirane (393 g) is further reacted without additional purification.

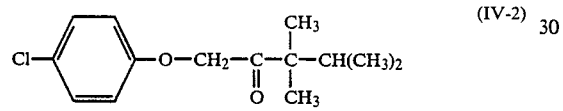
(IV-2)

461.5 9 (2.84 mols) of 1-chloro-3,3,4-trimethylpentan-2-one are added with stirring over the course of 1 hour to a mixture of 364.9 g (2.84 mols of 4-chlorophenol and 392 g (2.84 mols of potassium carbonate heated to 100° C. in 2,700 ml of N,N-dimethylformamide. After heating at 100° C. for ten hours, the mixture is cooled to 20° C., precipitated potassium chloride is removed by filtration, and the filtrate is evaporated under reduced pressure. The residue is taken up in 1,500 ml of dichloromethane and washed twice with 750 ml of 5% strength aqueous sodium hydroxide solution and 750 ml of water each time. After drying the organic phase over anhydrous sodium sulphate, the solvent is removed by distillation under reduced pressure and the oily residue is distilled in vacuo. 632 g (87.4% of theory) of 1-(4-chlorophenoxy)-3,3,4-trimethylpentan-2-one of boiling point 147°-148° C./0.15 torr are thus obtained.

The substances shown in the following example are also prepared according to the method given in Example 2:

Example 3

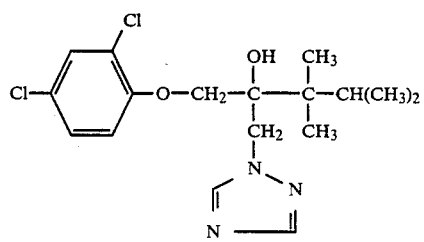
(I-3)

$n_D^{25} = 1.5363$

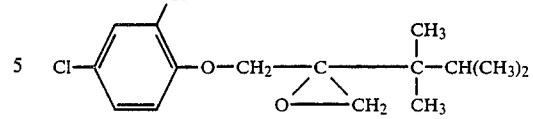
(II-3)

The oxirane is reacted further without additional purification.

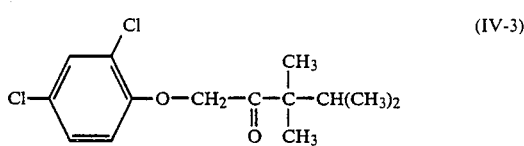
(IV-3)

The ketone is reacted further as a crude product without further purification.

Example 4

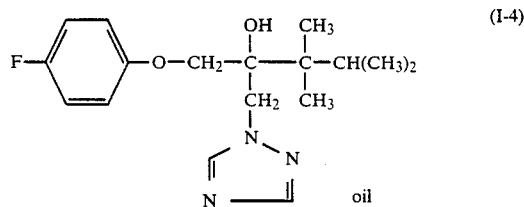
(I-4)

oil

The compounds shown below were employed as comparative substances in the following use examples:

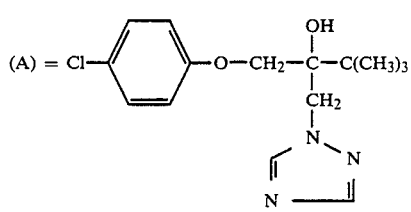

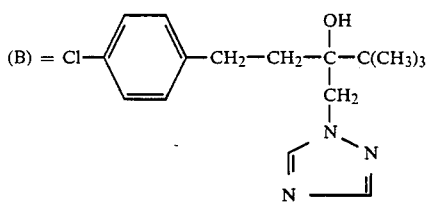

Example A

Venturia test (apple)/protective

Solvent: 4.7 parts by weight of acetone;
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the compound of the formula (I-1) according to the invention shows a very good action.

Example B

Sphaerotheca test (cucumber) / protective

Solvent 4.7 parts by weight of acetone;
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus Sphaerotheca fuliginea.

The plants are then placed in a greenhouse at 23° to 24° C. and at a relative atmospheric humidity of about 75%.

Evaluation is carried out 10 days after the inoculation.

In this test, the compound of the formula (I-2) according to the invention exhibits a better action than the comparative substance (A).

Example C

Erysiphe test (barley)/protective

Solvent: 100 parts by weight of dimethylformamide;
Emulsifier: 0.25 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compound of the formula (I-1) according to the invention shows a very good action.

Example D

Puccinia test (wheat) / protective

Solvent 100 parts by weight of dimethylformamide;
Emulsifier: 0.25 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita in a 0.1% strength aqueous agar solution. After the spore suspension has dried on, the plants are sprayed with the preparation of active compound until dew-moist. The plants remain in an incubation cabin at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, the compound of the formula (I-1) according to the invention shows a very good action.

Example E

Cochliobolus sativus test (barley) / protective

Solvent: 100 parts by weight of dimethylformamide;
Emulsifier: 0.25 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are sprayed with a conidia suspension of Cochliobolus sativus. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, the compound of the formula (I-1) according to the invention shows a very good action.

Example F

Leptosphaeria nodorum test (wheat)/protective

Solvent: 100 parts by weight of dimethylformamide;
Emulsifier: 0.25 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, the compounds of the formulae (I-1) and (I-2) according to the invention exhibit a better action than the comparative substances (A) and (B).

Example G

Pyrenophora teres test (barley)/protective

Solvent: 100 parts by weight of dimethylformamide;
Emulsifier: 0.25 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are sprayed with a conidia suspension of Pyrenophora teres. The plants then remain in an incubation cabin at 20° C. and 100% relative atmospheric humidity for 48 hours.

The plants are placed in a greenhouse at a temperature of about 20° C. and a relative atmospheric humidity of about 80°.

Evaluation is carried out 7 days after the inoculation.

In this test, the compound of the formula (I-1) according to the invention exhibits a very good action.

Example H

Pellicularia test (rice)

Solvent: 12.5 parts by weight of acetone;
Emulsifier: 0.3 parts by weight of alkylaryl polyglycol ether.

To produce a suitable preparation of active compound, 1 part by weight of active compound is mixed with the stated amount of solvent, and the concentrate is diluted with water and the stated amount of emulsifier to the desired concentration.

To test for activity, young rice plants in the 3- to 4-leaf stage are sprayed until dripping wet. The plants remain in a greenhouse until they have dried off. The plants are then inoculated with Pellicularia sasakii and are placed at 25° C. and 100% relative atmospheric humidity.

The evaluation of the disease infestation is carried out 5 to 8 days after the inoculation.

In this test, the compound of the formula (I-1) according to the invention exhibits a very good action.

Example I

Pyricularia test (rice)/protective

Solvent: 12.5 parts by weight of acetone;
Emulsifier: 0.3 parts by weight of alkylaryl polyglycol ether.

To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, the compound of the formula (I-1) according to the invention exhibits a better action than the comparative substance (B).

Example K

Plant tolerance test

Test plant: cucumber;
Duration of the test 7 days;
Solvent: 4.7 parts by weight of acetone;
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

Young plants are sprayed with this preparation of active compound until dripping wet and are placed in a greenhouse at about 20° C.

The plants are evaluated for damage, such as impairment of growth, discoloration and necroses.

In this test, the compounds of the formulae (I-1) and (I-2) according to the invention exhibit a better tolerance than the comparative substances (A) and (B).

It will be appreciated that the instant specification and claims are set forth by way of illustration and not limitation, and that various modifications and changes may be made without departing from the spirit and scope of the present invention.

We claim:

1. The compound 1-(4-chlorophenyl)-3-(1,2,4-triazol-1-yl-methyl)-4,4,5-trimethyl-hexan-3-ol of the formula

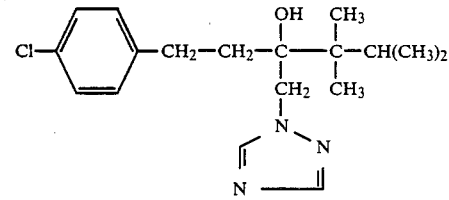

or an addition product thereof with an acid or metal salt.

2. A fungicidal composition comprising a fungicidally effective amount of a compound or addition product thereof according to claim 1 and an inert diluent.

3. A method of combating fungi which comprises applying to such fungi or to a fungus habitat a fungicidally effective amount of a compound or addition product thereof according to claim 1.

4. A plant growth-regulating composition comprising a plant growth-regulating effective amount of a compound or addition product thereof according to claim 1 and an inert diluent.

5. A method of regulating the growth of plants which comprises applying to such plants or to a habitat in which such plants are growing or are to be grown a plant growth-regulating effective amount of a compound or addition product thereof according to claim 1.

* * * * *